(12) United States Patent
Wagner

(10) Patent No.: US 7,231,808 B2
(45) Date of Patent: Jun. 19, 2007

(54) METHOD AND APPARATUS FOR MEASURING OXYGEN CONTENT

(76) Inventor: Ernst Wagner, Posener Strasse 1, 29308 Wisen/Aller (DE)

( * ) Notice: Subject to any disclaimer, the term of this patent is extended or adjusted under 35 U.S.C. 154(b) by 0 days.

(21) Appl. No.: 10/500,437

(22) PCT Filed: Oct. 17, 2002

(86) PCT No.: PCT/EP02/11648

§ 371 (c)(1),
(2), (4) Date: Mar. 11, 2005

(87) PCT Pub. No.: WO03/056325

PCT Pub. Date: Jul. 10, 2003

(65) Prior Publication Data

US 2005/0155407 A1    Jul. 21, 2005

(30) Foreign Application Priority Data

Dec. 28, 2001 (DE) ................. 101 64 293

(51) Int. Cl.
*G01N 7/00* (2006.01)
(52) U.S. Cl. ............. 73/31.02; 340/577; 169/44; 169/45
(58) Field of Classification Search ........ 73/31.02, 73/31.03; 169/44, 45; 340/577
See application file for complete search history.

(56) References Cited

U.S. PATENT DOCUMENTS

| 3,893,514 | A | * | 7/1975 | Carhart et al. ............ 169/46 |
| 3,984,826 | A | | 10/1976 | Kowalsky |
| 4,177,787 | A | * | 12/1979 | Hattori et al. ............ 123/198 D |
| 5,267,897 | A | * | 12/1993 | Drees ............ 454/225 |
| 5,552,775 | A | | 9/1996 | Harley |
| 5,844,148 | A | | 12/1998 | Klein et al. |
| 5,976,010 | A | * | 11/1999 | Reese et al. ............ 454/229 |
| 6,131,439 | A | * | 10/2000 | Hamburg et al. ........ 73/23.32 |
| 6,166,647 | A | * | 12/2000 | Wong ............ 340/628 |
| 6,601,653 | B2 | * | 8/2003 | Grabow et al. ............ 169/16 |
| 6,672,397 | B2 | * | 1/2004 | Taylor ............ 169/12 |
| 2002/0040940 | A1 | * | 4/2002 | Wagner et al. ............ 239/208 |

FOREIGN PATENT DOCUMENTS

| DE | 198 11 851 C2 | 9/1999 |
| DE | 198 50 564 A1 | 5/2000 |
| DE | 100 18 991 A | 10/2001 |
| EP | 0 924 504 A2 | 6/1999 |
| EP | 10 30 2 75 A2 | 8/2000 |
| EP | 1 092 979 A2 | 4/2001 |

* cited by examiner

*Primary Examiner*—Hezron Williams
*Assistant Examiner*—Ryan Christensen
(74) *Attorney, Agent, or Firm*—Bell Boyd & Lloyd LLP

(57) ABSTRACT

A method and apparatus for measuring the oxygen content in a closed target space, particularly for monitoring inertization levels in an inert gas device for fire prevention and/or fire extinguishing. Toward the aim of proposing a method for measuring the oxygen content in a target space with which an effective, certain, and representative determination of the oxygen concentration can be achieved for an optimally small expenditure in instrumentation and signal processing, the method provides that air samples are drawn from the target space and the oxygen concentration of the air samples is determined. An apparatus is equipped with a suction pipe system for sucking the air sample from the target space through various holes so that it can carry out the method.

15 Claims, 2 Drawing Sheets

METHOD AND APPARATUS FOR MEASURING OXYGEN CONTENT

BACKGROUND

The present invention relates to a method for measuring the oxygen content in a sealed target space, particularly for monitoring inertization levels in an inert gas device for fire prevention and/or fire extinguishing, and to a device for carrying out the method.

In closed rooms containing equipment that is sensitive to water, such as DP areas, electrical switching and distribution rooms, or storage areas containing high-value goods, what are known as inertization methods are increasingly being utilized to reduce the risk of fires and to extinguish them. The extinguishing effect produced by this technique is based on the principle of oxygen displacement. As is generally known, normal ambient air consists of 21% oxygen, 78% nitrogen, and 1% other gasses by volume. In order to extinguish and prevent fires, the inert gas concentration in the relevant space is elevated, and so the proportion of oxygen is reduced, by infusing an inert gas such as pure nitrogen that displaces oxygen. Many substances no longer burn when the oxygen level drops below 15–18% by volume. It may be necessary to lower the oxygen level further to 12%, for example, depending on the combustible materials in the relevant room.

Some known systems employ an inertization method with which a fire can be effectively extinguished given an optimally small storage capacity for the flasks of inert gas. According to this method, the oxygen content in the closed room is lowered to a base inertization level, (e.g., 16%) and in the event of fire, a very rapid full inertization occurs (e.g., an inertization of 12% or lower).

An inert gas device for fire prevention and/or fire extinguishing for carrying out the cited inertization method includes the following components: an oxygen meter for measuring the oxygen content in the monitored target space; a fire detector for detecting a combustion parameter in the air of the target space; a control for evaluating the data of the oxygen meter and the combustion parameter detector and controlling the running of the inertization process; and an apparatus for producing inert gas and abruptly infusing it into the target space.

The term combustion parameter refers to physical quantities that underlie measurable changes in the environment of an incipient fire (e.g., the ambient temperature, the proportion of solids, liquids, or gas in the ambient air (formation of smoke in the form of particulates, aerosols, or vapor) or the ambient radiation).

The oxygen meter serves for setting the base inertization level in the target space. If a threshold oxygen concentration value is exceeded, such as due to a leak in the target space, the control sends a command to a separate system to infuse inert gas into the space, so that the oxygen proportion is reduced. The oxygen meter signals when the threshold value of the base inertization level has been reached again. The position of the base inertization level therein depends on properties of the room. But if the detector for combustion parameters senses a combustion parameter, however, the system receives a command to flood the room with inert gas until the oxygen concentration in the target space is reduced to a specified full inertization level.

The measuring of the oxygen content in the target space is important for a reliable control of the method in this type of inert gas device for fire prevention and/or fire extinguishing. According to the prior art, the oxygen concentration in the target space is measured by point shaped oxygen sensors, which transmit the measurement values of the oxygen content to the control in the form of an analog signal. It is common to utilize 4–20 mA current interfaces, where 4 mA corresponds to a concentration of 0% oxygen, and 20 mA corresponds to the end of the measurement range (e.g., 25% oxygen). The disadvantage of utilizing point shaped oxygen sensors is that a greater number of such sensors are needed in the target space in order to get a representative reading of the oxygen content in the air in the room. That requires correspondingly costly cable connections between the individual sensors that are distributed in the target space and the actual control. Furthermore, the control requires a correspondingly high number of analogous interfaces. This requires a particularly large and particularly expensive hardware outlay.

An exceptionally disadvantageous aspect turns out to be that the control must continuously process a large number of signals. In particular, forming average values, estimating errors, and comparing to preset threshold values require routines, which are absolutely indispensable for controlling the inertization process. Only with the aid of the processed data of the oxygen sensors is it possible to drive the system for infusing inert gas, a fresh air supply, or a fan for air circulation in the target space. The signal processing in the control is therefore very intensive and requires a high complexity of software.

SUMMARY

The present invention proposes a method for measuring the oxygen content in a target space with which it is possible to determine the oxygen concentration effectively, reliably, and in representative fashion, and with an optimally small outlay for instrumentation and signal processing. This is achieved by a method for measuring oxygen content including taking an air sample from the target space by means of a series of suction holes of a suction pipe system, so that the oxygen concentration of the air sample can then be determined by means of an oxygen detector.

The present invention provides a number of benefits for measuring the oxygen content in a target space. Air samples from various suction holes are mixed by suction through holes in the suction pipe system. Thus, the oxygen concentration of the air sample automatically corresponds to an average value of the oxygen concentration of the target space, and the costly average value formation is omitted from the signal processing in a control. In a simpler embodiment, software for evaluating the measurement values can even be omitted. Furthermore, the monitored volume (i.e., the measured volume), is substantially larger than in the case of oxygen sensors that are configured in points as in the prior art. This brings particular cost advantages in the purchasing, installation, and maintenance of the device for measuring the oxygen content in the target space and ultimately of the overall inert gas device for fire prevention and/or fire extinguishing.

The present invention also includes a device for carrying out the above method that includes at least one suction pipe system for drawing an air sample from the monitored target space through various holes. The device realizes the combination of the inventive method with an oxygen meter in an ideal fashion. Benefits are gained particularly by the ability to forgo the utilization of a plurality of point shaped oxygen sensors in the target space. Instead, at least one suction pipe system is provided for drawing an air sample from the monitored target space through various suction holes. That way, complicated cable connections between the former point shaped oxygen sensors and the control can also be omitted. An analog interface must still be provided in the control for the oxygen meter, but this can be realized with a small hardware outlay. Furthermore, the signal processing in the control is substantially simpler, since it is no longer necessary to process a large number of signals from individual oxygen sensors. As a result, the software for signal processing can also be constructed correspondingly simple. It is therefore possible to measure the oxygen content at little expense in terms of instrumentation and signal processing, which brings economic benefits particularly in the purchase and maintenance of the inert gas system as a whole.

Following the determination of the oxygen concentration of the drawn air sample by the oxygen sensor, the oxygen measuring method includes comparing the measurement value of the oxygen concentration of the air sample to fixed threshold values in the oxygen sensor, and, in the case where the fixed threshold value is exceeded, reducing the oxygen concentration by infusing inert gas into the target space. Thus, the inertization method is adapted for possible leaks in the target space by means of the continuous measuring of the oxygen content. A benefit of this development is the existence of a separate "intelligence," so to speak, in the inventive oxygen measuring method, in the sense that the method performs a comparison with predetermined threshold values of its own accord. A signal is sent to the control in a central unit only when a threshold value is crossed. This substantially reduces, not only the data traffic between the device for carrying out the inventive oxygen measuring method and the control of the inert gas device for fire prevention and/or fire extinguishing, but also substantially reduces the signal processing in the control. With this "distributed intelligence," signal processing can be divided between the control and the oxygen sensor that is connected to it. This makes possible a substantial reduction in the software outlay, and particularly the purchase price and the maintenance outlay of the control of an inert gas device for fire prevention and/or fire extinguishing.

A detector for fire parameters may be utilized in the disclosed method for measuring the oxygen content in the target space. This detector sends a signal for full inertization in the event of fire. This development represents the procedural implementation of the combining of a known aspirative fire detector with the inert gas extinguishing technique. An aspirative fire detector is a fire detector that actively draws a representative subvolume of air from the room at a number of locations via a suction pipe system, conduit system, or duct system and then conducts these subvolumes to a detector for detecting a fire parameter. With the integration of the detector of fire parameters into the device for carrying out the disclosed method, an aspirative fire detector is created in addition to the oxygen measuring device. It is beneficial that existing components can be accessed for realizing this aspirative fire detector. The target space can thus be equipped with an aspirative fire detector, thereby improving the fire detection, without additional outlay.

In another example of the disclosed method, the fire parameters sensed by the detector are smoke in the form of particulates, aerosols, or vapor, and at least one combustion gas. That way, the fire detector that is equipped with the disclosed oxygen meter reacts with particular sensitivity to the parameters that are typical of a fire. A fire can thus be detected in its incipient stage, and the inert gas device for fire prevention and/or fire extinguishing can be alarmed.

One example of the inventive oxygen meter provides that the combustion gas that is sensed in the detector is CO or $CO_2$. The advantage of this embodiment in particular is that the fire detector is especially sensitive to fire parameters and is also able to distinguish between an actual fire and cigarette smoke or other smoke-like quantities that are not characteristic of fire. Alternative embodiments are of course also imaginable.

In another example, the measurement of the air quality by a CO or $CO_2$ sensor is integrated into the method, and the fresh air supply of the target space is controlled in dependence on the signal of the CO or $CO_2$ sensor. The advantages that are discussed above in connection with the oxygen sensor are also brought to bear here. In particular, this advantageous embodiment forgoes the utilization of a plurality of CO or $CO_2$ sensors that are distributed in the target space and that measure pointwise, as well as the correspondingly large hardware and software outlay in the control for processing the signals.

Yet another example determines the oxygen concentration by means of a reference oxygen sensor. This is done independently from the measuring of the above cited oxygen sensor. The reference oxygen sensor is permanently disposed in the air stream of the air sample that is drawn. For example, the reference oxygen sensor could be located in the immediate vicinity of the oxygen sensor. The measurement value of the oxygen concentration that is acquired by means of the reference oxygen sensor is then compared to the measurement value of the oxygen concentration that was registered at the same time by the oxygen sensor in the air stream. It is provided that a disturbance signal is emitted if the comparison of the two measurement signals indicates that the oxygen concentration value that was acquired by the oxygen sensor deviates from the oxygen concentration value acquired by the reference oxygen sensor deviates more than a previously defined tolerance value. The comparison of measurement values and the output of the disturbance signal can occur in and by means of the oxygen sensor or the reference oxygen sensor. Alternative solutions are of course also imaginable.

In another example, it is further provided that the reference oxygen sensor, as opposed to the oxygen sensor, is normally off. The reference oxygen sensor is switched on at regular intervals, such as once a day or once a week. Following activation, a minimum heating time is allowed to pass before the oxygen concentration in the air stream is determined. The activation process could occur with the aid of a signal that is generated by a clock timer. On the other hand, it would also be imaginable for the activation to occur at the push of a button, for instance in maintenance operations. Premature aging of the reference oxygen sensor can be prevented particularly easily by its being on only temporarily.

It is particularly beneficial when the disturbance signal, which is output when the comparison of the two measurement values indicates that the oxygen concentration value acquired by the oxygen sensor deviates from the oxygen concentration value acquired by the reference oxygen sensor by more than a previously defined tolerance value, is utilized to the effect that the reference oxygen sensor remains on permanently and, therefore, continuously delivers measurement values of the oxygen concentration of the drawn air sample. These measurement values are then evaluated instead of those of the oxygen sensor. Measurement uncertainties that are caused by the aging of the oxygen sensor when it is continuously driven can thus be eliminated.

According to an example of a device, inertization levels in the target space are set by a control, which also controls the fresh air supply and a fan, whereby at least one oxygen sensor is provided for measuring the oxygen concentration in an air sample that is drawn from the target space, and at least one detector is provided for detecting fire parameters in an air sample drawn from the target space by one of the suction pipe systems. Such a device is particularly easy to realize, in which the measuring components that are utilized in the inert gas device for fire prevention and/or fire extinguishing are utilized only for analyzing the air sample drawn from the target space.

At least one CO or $CO_2$ sensor for measuring the air quality in an air sample drawn from the target space by one of the suction pipe systems is expediently provided. Thus, the air quality can also be monitored by the inventive inert gas device for fire prevention and/or fire extinguishing.

An oxygen sensor and a detector for detecting fire parameters and/or a CO or $CO_2$ sensor are integrated in a suction pipe system. The number of components that are utilized in the inert gas device for fire prevention and/or fire extinguishing can thus be reduced. This brings additional economic benefits in the purchase, installation and maintenance of an inert gas device for fire prevention and/or fire extinguishing.

In an example, electrochemical cells consisting of zirconium dioxide are utilized as oxygen sensors. Zirconium dioxide based oxygen sensors are known from automotive technology, where they are used in catalytic converters to measure the oxygen content in exhaust gasses. The sensors are considered reliable, sensitive, sturdy and low-maintenance components. The disclosed device can be realized particularly cost-effectively if standard components are utilized in the inventive device.

In a further example, it is provided that, besides the oxygen sensor, a reference oxygen sensor is utilized for measuring the oxygen concentration of the air sample that is drawn from the target space. This serves as a reference relative to the oxygen sensor and lies continuously in the air stream, though the sensor is normally off. This prevents the aging of the reference oxygen sensor. The sensor is activated at regular intervals (e.g., once a day or once a week). The signal for activating the reference sensor is generated by a clock timer, for example. It can also be generated at the push of a button, for instance for maintenance operations. Following the activation of the reference oxygen sensor, the minimum heating time is allowed to pass. Then the two measurement values of the oxygen sensor and the reference sensor are compared. If the difference between the two values is larger than a predetermined threshold, a disturbance is signaled, and the reference oxygen sensor is no longer switched off. Its measurement values are evaluated instead of those of the aged oxygen sensor.

DETAILED DESCRIPTION OF THE PRESENT EXAMPLES

Figure 1:
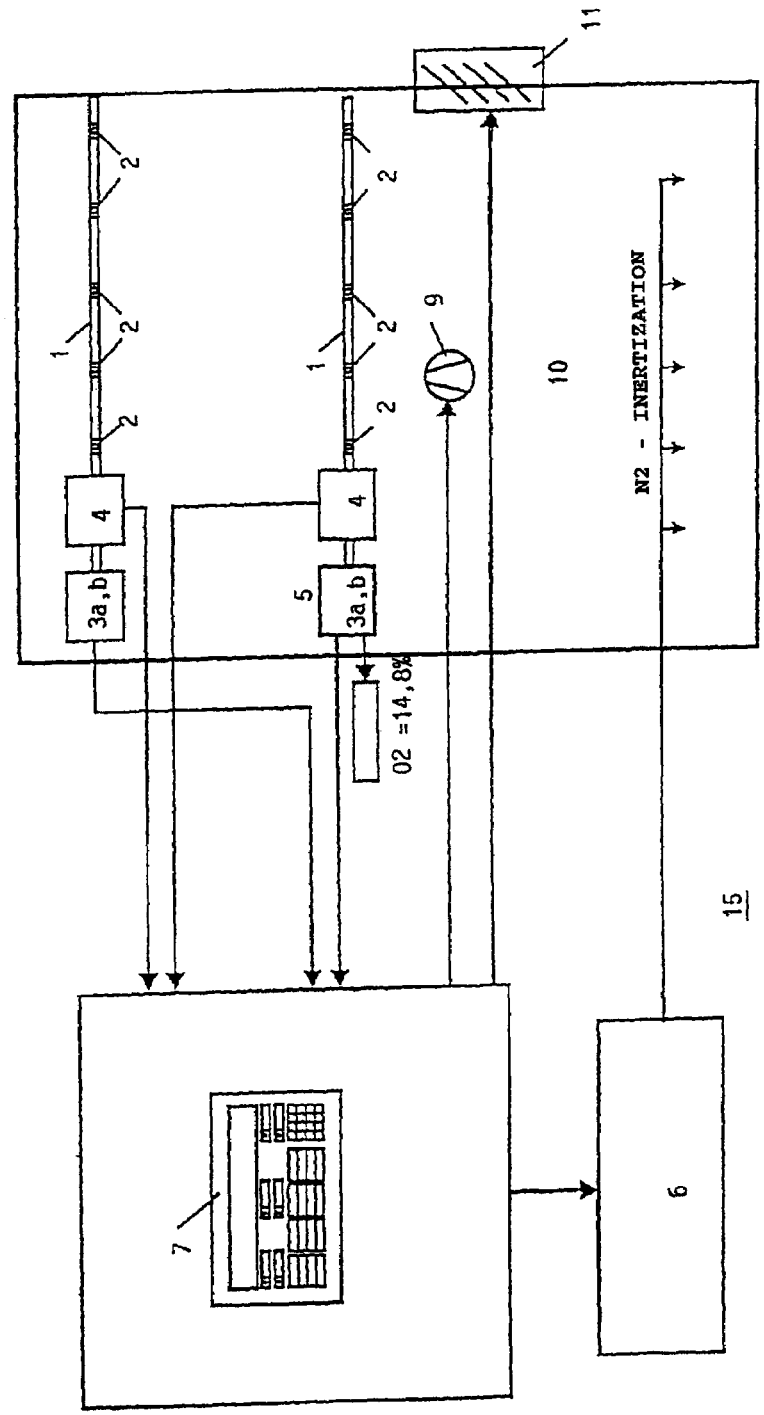
FIG. 1 illustrates a schematic block diagram of a device for measuring the oxygen content in an inert gas device for fire prevention and/or fire extinguishing.

FIG. 1 represents a schematic block diagram of a device for measuring the oxygen content in an inert gas device for fire prevention and/or fire extinguishing 6. The inert gas device for fire prevention and/or fire extinguishing 6 serves to prevent and extinguish fires in the closed target space 10.

Two suction pipe systems 1 for sucking air samples through various holes 2 are provided in the target space 10. The suction pipe systems 1 are each equipped with a suction sensor 8 in which the air samples from the target space 10 are conducted to an oxygen sensor 3 and to a detector 4 for detecting fire parameters, namely a CO or $CO_2$ sensor 5. In the device of FIG. 1, two suction pipe systems 1 are represented, one of which is mounted below the ceiling of the target space 10 at a distance of up to 1 m therefrom as warranted, and the other of which is mounted at breathing height, i.e., approximately 1.5 m above the floor.

The oxygen sensor 3a determines the oxygen concentration of the respective air sample and compares the measurement value to fixed threshold values. If a fixed threshold value is exceeded, the oxygen sensor 3a sends a signal to a control 7 over a data line, which effectuates an infusion of inert gas into the target space 10 and a reduction of the oxygen concentration. For that purpose, the control 7 signals an apparatus for producing and infusing inert gas 6 to perform an inertization of the target space 10.

Based on the continuous drawing of air samples from the target space 10 by the aspirative suction device, the oxygen content of the air in the room is continuously measured in the oxygen sensor 3a. As soon as the oxygen concentration of the continuously drawn air sample in the oxygen sensor 3a matches a fixed threshold value, the control 7 receives a corresponding signal to discontinue inertization.

In the example represented in FIG. 1, in addition to smoke in the form of particulates, aerosols, or vapor, at least one combustion gas such as CO or $CO_2$ is also sensed in the detector 4 for detecting fire parameters. By utilizing at least two different fire parameters that can independently establish the presence of a fire in the target space 10, it is possible to realize an optimal redundancy and a corresponding fail-safety of the inert gas device for fire prevention and/or fire extinguishing 6. In particular, the detector 4 is also able to distinguish between an actual fire and cigarette smoke or similar smoke-like quantities that are not characteristic of fire.

In another suction pipe system 1 according to FIG. 1, a CO or $CO_2$ sensor 5 and a detector 4 for detecting fire parameters are integrated in the suction sensor. The CO or $CO_2$ sensor 5 monitors the air quality of the target space 10 by determining the CO or $CO_2$ content of the air sample that is drawn by the suction pipe system. If the air quality of the target space 10 no longer corresponds to the expected standards, the sensor 5 signals this to the central control 7, which drives a fan 9 for air circulation, or respectively, fresh air supply 11. If a sufficiently improved air quality is subsequently measured, the fan 9 or fresh air supply 11 then switches off again.

It is also possible to integrate several different sensors in a suction sensor 8, for instance a CO or $CO_2$ sensor 5 in combination with a detector 4 for detecting fire parameters but also an oxygen sensor 3a in combination with one of the other sensors 4 or 5 cited above.

Besides the oxygen sensor 3a, a reference oxygen sensor 3b may be also utilized for measuring the oxygen concentration of the air sample drawn from the target space 10. This serves as a reference relative to the oxygen sensor 3a and lies in the air stream at all times but is normally switched off. This prevents the aging of the reference oxygen sensor 3b. The sensor 3b is switched on at regular intervals (e.g., once a day or once a week). The signal for switching on the reference oxygen sensor 3b is generated by a clock timer. It can also be generated at the push of a button, for instance in maintenance operations. Following the activating of the reference oxygen sensor 3b, a minimum heating time is allowed to pass. The two measurement values of the oxygen sensor 3a and the reference sensor 3b are then compared. If the difference between the two measurement values is greater than a defined threshold, a disturbance is signaled, and the reference oxygen sensor 3b is no longer switched off. Its measurement values are evaluated instead of those of the aged oxygen sensor 3a.

Figure 2:
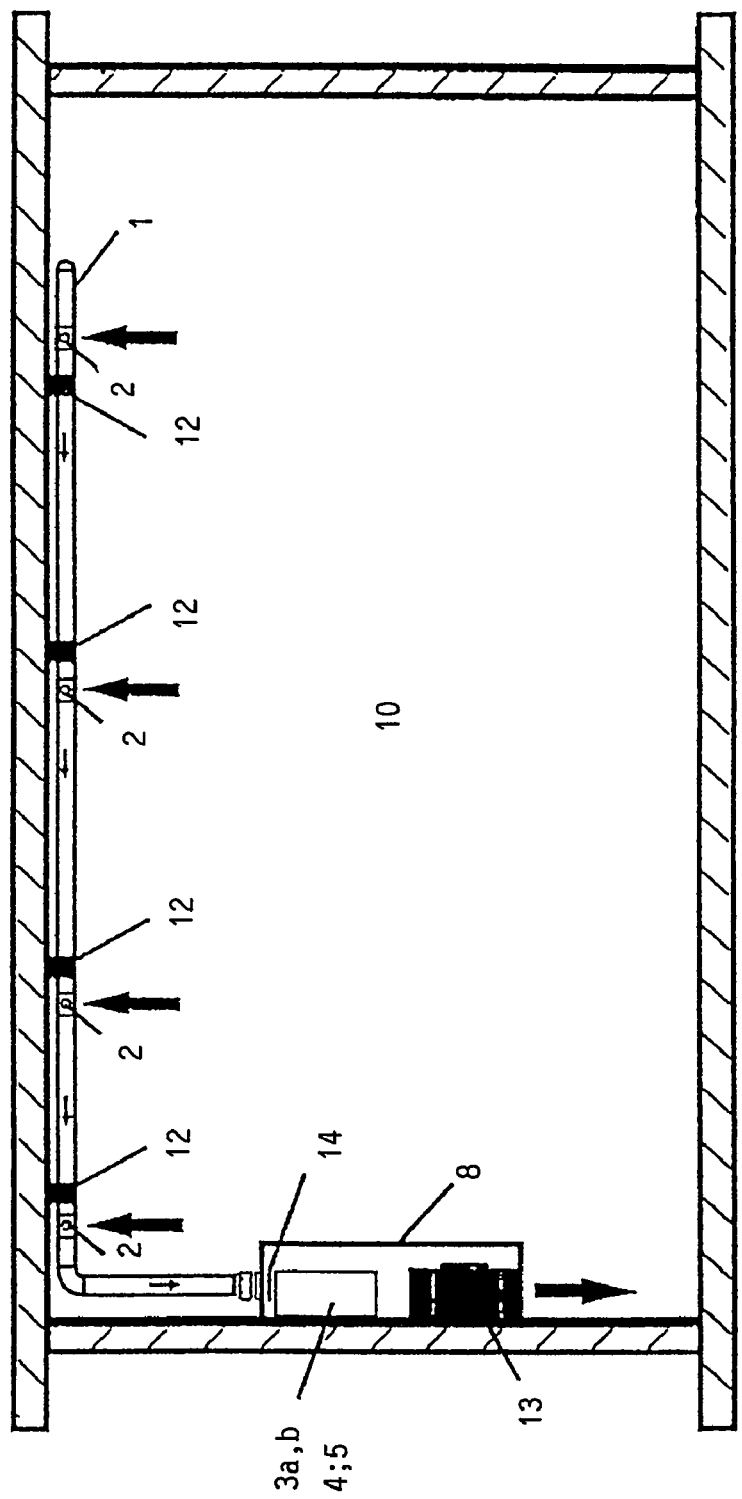
FIG. 2: illustrates a schematic representation of a device for measuring the oxygen content in a closed target space.

FIG. 2 is a schematic representation of another exemplary device for measuring the oxygen content in a closed room 10. In this example, the suction pipe system 1 is attached beneath the ceiling of the target room 10 by means of pipe straps 12. Air is drawn from the target space 10 through the holes 2 in the suction pipe system 1. To that end, a suction unit 13 that is integrated in the suction sensor 8 is utilized. The suction unit 13 and the suction pipe system 1 are monitored by means of an air stream sensor 14 which is disposed at the end of the suction pipe system 1.

After passing the air stream sensor 14, the air sample passes the oxygen sensor 3a. The oxygen sensor 3a measures the oxygen concentration of the air sample, which represents an average value of the oxygen concentration of the air of the target space 10. The average value is compared to threshold values in the oxygen sensor 3a. If the threshold values are exceeded, the oxygen content in the air of the target space 10 is too high to prevent a fire reliably. At the appearance of the signal over a first threshold value, the control 7 drives the device that generates the inert gas and infuses the inert gas into the target space 10 (i.e., a generator).

If the oxygen content continues to rise, this indicates a defective generator that cannot infuse inert gas into the space 10. At the appearance of the signal over a second threshold value, the control 7 signals disturbance.

If the values are below the threshold values, a full inertization is not triggered. At the appearance of the signal under a first threshold value, the control 7 stops the generator because the desired oxygen content has been achieved.

If the oxygen content continues to drop, this indicates a defective generator that is no longer stopping the infusion of inert gas into the target space 10. At the appearance of the signal below a second threshold value, the control 7 signals disturbance.

If the oxygen content falls below a value that is dangerous to humans, personal safety measures are initiated. At the signal below a third threshold value, the control 7 triggers personal safety measures such as the evacuation of the room or the blocking of entry.

Instead of the oxygen sensor 3a, a CO or $CO_2$ sensor 5 and/or a detector 4 for detecting fire parameters can be utilized in the suction sensor 8.

Although preferred examples of the methods and apparatus have been disclosed for illustrative purposes, those of ordinary skill in the art will appreciate that the scope of this patent is not limited thereto. On the contrary, this patent covers all methods and apparatus found within the scope of the appended claims.

The invention claimed is:

1. A method for measuring the oxygen content in a closed target space for monitoring inertization levels in an inert gas device for controlling fire, the method comprising the steps of:
    drawing an air sample from the target space with one or more suction holes of a suction pipe system;
    determining a first measurement value of the oxygen concentration in the drawn air sample using an oxygen sensor;
    determining a second measurement value of the oxygen concentration in the drawn air sample using a reference oxygen sensor, wherein the reference oxygen is switched on at regular time intervals during the step of determining the second measurement value to prevent aging of the reference oxygen sensor;
    comparing the first measurement value to the second measurement value; and
    issuing a disturbance signal from one of the oxygen sensor or the reference oxygen sensor when deviation of the first measurement value from the second measurement value exceeds a predetermined amount.

2. A method as defined in claim 1, further comprising:
    comparing, in the oxygen sensor, the first measurement value of the oxygen concentration of the air sample to a fixed threshold value; and
    lowering the oxygen concentration by the infusion of inert gas into the target space when the threshold value is exceeded.

3. A method as defined in claim 1, further comprising:
    measuring fire parameters in the drawn air sample with a detector; and
    sending a signal from the detector for full inertization of the target space when a fire parameter is detected.

4. A method as defined in claim 3, wherein the fire parameters that are detected in the detector include at least one of smoke in the form of particulates, aerosols, vapor, and at least one combustion gas.

5. A method as defined in claim 4, wherein the combustion gas detected in the detector is CO or CO2.

6. A method as defined in claim 1, further comprising:
    monitoring CO and/or CO2 content in the drawn air sample with a CO and/or CO2 sensor; and
    supplying fresh air to the target space dependent on a measurement value of the CO and/or CO2 content.

7. A method as defined in claim 2, further comprising:
    following the issuing of the disturbance signal, continuously determining the oxygen concentration in the air sample with the reference oxygen sensor, whereupon additional evaluation of the first measurement value of the oxygen concentration is performed with the aid of the second measurement value that is determined by the reference oxygen sensor instead of the first measurement value determined by the oxygen sensor.

8. An apparatus measuring the oxygen content in a closed target space of an inert gas device for controlling fire in a closed room, the apparatus comprising:
    an inert gas device;
    at least one suction pipe system configured to suck an air sample from the target space through various holes;
    an oxygen sensor to measure oxygen concentration in the air sample that is drawn from the target space and determine a first measurement value; and
    a reference oxygen sensor that measures oxygen concentration in the air sample that is drawn from the target space and determines a second measurement value to be used as a reference relative to the first measurement value of the oxygen sensor, said reference oxygen sensor being switched on at regular intervals for the second measurement to prevent aging of the reference oxygen sensor,
    wherein, if the measured value for the oxygen concentration of the oxygen sensor deviates from the measured value of the oxygen concentration of the reference oxygen sensor by a preset value, one of the oxygen sensor and the reference oxygen sensor transmits an alarm signal.

9. An apparatus as defined in claim 8, wherein at least one of the oxygen sensor and the reference oxygen sensor is integrated in the at least one suction pipe systems.

10. An apparatus as defined in claim 8, further comprising:
   a fan and fresh air supply;
   a control that is configured to set inertization levels in the target space, and control the fresh air supply and fan; and
   at least one detector to detect fire parameters in an air sample that is drawn from the target space by the at least one suction pipe system.

11. An apparatus as defined in claim 8, wherein at least one detector is integrated in the at least one suction pipe system.

12. An apparatus as defined in claim 8, further comprising:
   at least one CO or CO2 sensor to measure the air quality in an air sample that is drawn from the target space by the at least one suction pipe system.

13. An apparatus as defined in claim 12, wherein at least one of the CO or CO2 sensors is integrated in the at least one suction pipe system.

14. An apparatus as defined in claim 8, wherein the oxygen sensors comprise electrochemical cells of zirconium dioxide.

15. A method for measuring the oxygen content in a closed target space for monitoring inertization levels in an inert gas device, the method comprising the steps of:
   drawing an air sample from the target space with one or more suction holes of a suction pipe system;
   monitoring CO and/or CO2 content in the drawn air sample with a CO and/or CO2 sensor; and
   determining a first measurement value of the oxygen concentration in the drawn air sample using an oxygen sensor;
   determining a second measurement value of the oxygen concentration in the drawn air sample using a reference oxygen sensor, wherein the reference oxygen is switched on at regular time intervals to prevent ageing of the reference oxygen sensor;
   comparing the first measurement value to the second measurement value;
   issuing a disturbance signal from one of the oxygen sensor or the reference oxygen sensor when deviation of the first measurement value from the second measurement value exceeds a predetermined amount; and
   supplying fresh air to the target space dependent on a measurement value of the CO and/or CO2 content.

* * * * *